United States Patent [19]

Mutsukado et al.

[11] Patent Number: 4,892,947

[45] Date of Patent: Jan. 9, 1990

[54] 3(2H)PYRIDAZINONE, PROCESS FOR ITS PREPARATION AND ANTI-ALLERGIC AGENT CONTAINING IT

[75] Inventors: Motoo Mutsukado, Sakura; Keizo Tanikawa, Tokyo; Ken-ichi Shikada, Kuki; Ryozo Sakoda, Kashiwa, all of Japan

[73] Assignee: Nissan Chemical Industries Ltd., Tokyo, Japan

[21] Appl. No.: 854,521

[22] Filed: Apr. 22, 1986

[30] Foreign Application Priority Data

Apr. 27, 1985 [JP] Japan .................................. 60-91612

[51] Int. Cl.[4] ..................... C07D 237/22; A61K 31/50

[52] U.S. Cl. ..................................... 514/247; 544/241

[58] Field of Search .......................... 544/241; 514/247

[56] References Cited

U.S. PATENT DOCUMENTS 3,317,531 5/1967 Nachoneder ........................ 544/241
4,783,462 11/1988 Mutsukado .......................... 544/238

FOREIGN PATENT DOCUMENTS 784639 5/1968 Canada ................................ 544/241
0186817 7/1986 European Pat. Off. .
1670169 11/1970 Fed. Rep. of Germany ...... 544/241
1413955 8/1964 France ................................ 544/241
1170970 7/1985 U.S.S.R. .

OTHER PUBLICATIONS

Bourdais, Chem. Abs., 62, 2772(f), 1965.
Matsuo, Chemical Abstracts, vol. 89, 1978, p. 656, Abstract No. 24341a, Columbus, Ohio, U.S.; (1978).
Bulletin De La Societe Chimique De France, No. 9, 1964, pp. 2124–2132, Paris, Fr; J. Bourdais: "No. 342-Etudes en Serie Heterocyclique: III-Action des Amines Aliphatiques et Arylaliphatiques Sur Les Dihalogeno-4,5 (2h)-Pyridazinones-3" * pp. 2124, 2125, 2126(Table II), 2127*.

*Primary Examiner*—Maril L. Berch
*Attorney, Agent, or Firm*—Oblon, Spivak, McClelland, Maier & Neustadt

[57] ABSTRACT

A 3(2H)pyridazinone of the formula:

(I)

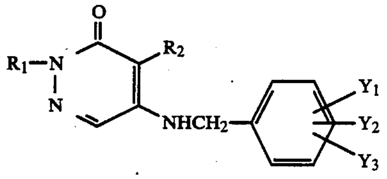

wherein $R_1$ is hydrogen, methyl, $C_3$-$C_6$ alkenyl, $C_5$ or $C_6$ cycloalkyl, benzyl, phenyl, $-(CH_2)_mCO_2R_3$ (wherein $R_3$ is hydrogen or $C_1$-$C_5$ alkyl, and m is an integer of from 1 to 4), $-(CH_2)_nA$ (wherein A is —OH or $-N(R_4)_2$ wherein $R_4$ is $C_1$-$C_3$ alkyl, and n is an integer of from 2 to 6) or $-CH_2CF_3$; $R_2$ is chlorine or bromine; each of $Y_1$ and $Y_2$ which may be the same or different, is hydrogen, $C_1$-$C_5$ alkyl, $C_2$-$C_8$ alkenyl, halogen, $-OR_5$ (wherein $R_5$ is hydrogen, $C_1$-$C_8$ alkyl or

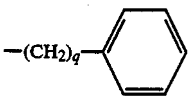

wherein q is an integer of from 1 to 4), $-CO_2R_6$ (wherein $R_6$ is hydrogen or $C_1$-$C_5$ alkyl), $-N(R_7)_2$ (wherein $R_7$ is $C_1$-$C_4$ alkyl) or $-SR_8$ (wherein $R_8$ is $C_1$-$C_4$ alkyl); and $Y_3$ is $C_1$-$C_5$ alkyl, $C_2$-$C_8$ alkenyl, halogen, $-OR_5$ (wherein $R_5$ is as defined above), $-CO_2R_6$ (wherein $R_6$ is as defined above), $-N(R_7)_2$ (wherein $R_7$ is as defined above) or $-SR_8$ (wherein $R_8$ is as defined above), or a pharmaceutically acceptable salt thereof.

29 Claims, No Drawings

3(2H)PYRIDAZINONE, PROCESS FOR ITS PREPARATION AND ANTI-ALLERGIC AGENT CONTAINING IT

The present invention relates to a 3(2H)pyridazinone which exhibits antagonism against slow reacting substance of anaphylaxis (SRS-A) which induces a contraction of bronchial smooth muscle, and thus is useful as an anti-allergic agent, a process for its preparation and a pharmaceutical composition containing it.

SRS-A is believed to be a principal etiologic substance which induces immediate allergy such as bronchial asthma or allergic rhinitis. Therefore, a medicine which controls the pharmacological effect of SRS-A, i.e. a SRS-A antagonist, is expected to be a useful anti-allergic agent.

However, a very few medicinal substances show antagonism against SRS-A, and no instance of their practical application has been reported.

As an example of a compound which is somewhat similar to the compound of the present invention, Canadian Patent 784,639 (hereinafter referred to as reference (a)) discloses 3(2H)pyridazinone derivatives having hydrogen, $C_1$–$C_8$ alkyl, phenyl or $C_3$–$C_8$ cycloalkyl at 2-position, chlorine or bromine at 4-position and benzylamino at 5-position. However, the usefulness of the compounds disclosed in this reference (a) is restricted to a herbicide, and no mention is made as to its medical use or pharmacological activities.

As another example of a compound similar to the compound of the present invention, Chemical Abstract, 62, 2773b, (Bull. Soc. Chim, France, 1964 (9) p 2124–32) (reference (b)) discloses 3(2H)pyridazinones having hydrogen or diethylaminoethyl at 2-position, chlorine at 4-position and benzylamino at 5-position. This reference (b) is silent about medical use or pharmacological activities.

Likewise, as still another example of a compound similar to the compound of the present invention, published German Patent Application No. 1670169 (published on Nov. 5, 1970) (reference (c)) discloses 3(2H)pyridazinones having hydrogen or an aliphatic, cycloaliphatic, araliphatic or aromatic group at 2-position, chlorine or bromine at 4-position and aralkylamino at 5-position. This reference (c) discloses a process for the synthesis of pyridazinones including such compounds, their application for agricultural chemicals, their application as intermediates for medicines or dyestuffs, or their application as intermediates for various compounds. However, no mention is made to their pharmacological activities, and no specific examples are given for such compounds. Further, such compounds are not specifically described.

The present inventors have synthesized and studied various compounds for antagonistic activities against SRS-A, and it has been surprisingly found that 3(2H)pyridazinones of the formula I and their pharmaceutically acceptable salts exhibit antagonistic activities against SRS-A and thus are useful as an active ingredient for an anti-allergic agent.

Namely, the present invention provides a 3(2H)pyridazinone of the formula:

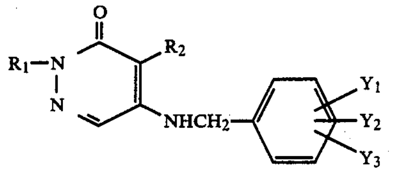

(I)

wherein $R_1$ is hydrogen, methyl, $C_3$–$C_6$ alkenyl, $C_5$ or $C_6$ cycloalkyl, benzyl, phenyl, $—(CH_2)_mCO_2R_3$ (wherein $R_3$ is hydrogen or $C_1$–$C_5$ alkyl, and m is an integer of from 1 to 4), $—(CH_2)_nA$ (wherein A is —OH or $—N(R_4)_2$ wherein $R_4$ is $C_1$–$C_3$ alkyl, and n is an integer of from 2 to 6) or $—CH_2CF_3$; $R_2$ is chlorine or bromine; each of $Y_1$ and $Y_2$ which may be the same or different, is hydrogen, $C_1$–$C_5$ alkyl, $C_2$–$C_8$ alkenyl, halogen, $—OR_5$ (wherein $R_5$ is hydrogen, $C_1$–$C_8$ alkyl or

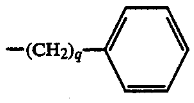

wherein q is an integer of from 1 to 4), $—CO_2R_6$ (wherein $R_6$ is hydrogen or $C_1$–$C_5$ alkyl), $—N(R_7)_2$ (wherein $R_7$ is $C_1$–$C_4$ alkyl) or $—SR_8$ (wherein $R_8$ is $C_1$–$C_4$ alkyl); and $Y_3$ is $C_1$–$C_5$ alkyl, $C_2$–$C_8$ alkenyl, halogen, $—OR_5$ (wherein $R_5$ is as defined above), $—CO_2R_6$ (wherein $R_6$ is as defined above), $—N(R_7)_2$ (wherein $R_7$ is as defined above) or $—SR_8$ (wherein $R_8$ is as defined above), or a pharmaceutically acceptable salt thereof.

Now, the present invention will be described with reference to the preferred embodiments.

Specific examples of substituents $R_1$, $R_2$, $Y_1$, $Y_2$ and $Y_3$ in the formula I will be described. However, it should be understood that the compounds of the formula I are not restricted by such specific examples. In the following substituents, "n" means normal, "i" means iso, "sec" means secondary, and "t" means tertiary.

$R_1$ includes hydrogen, methyl, allyl, 2-butenyl, 2-pentenyl, 2-hexenyl, cyclopentyl, cyclohexyl, benzyl, phenyl, carboxymethyl, 2-carboxyethyl, 3-carboxypropyl, 4-carboxybutyl, methoxycarbonylmethyl, ethoxycarbonylmethyl, n-propoxycarbonylmethyl, i-propoxycarbonylmethyl, n-butoxycarbonylmethyl, i-butoxycarbonylmethyl, t-butoxycarbonylmethyl, n-pentyloxycarbonylmethyl, 2-methoxycarbonylethyl, 2-ethoxycarbonylethyl, 2-n-propoxycarbonylethyl, 2-i-propoxycarbonylethyl, 2-n-butoxycarbonylethyl, 3-methoxycarbonylpropyl, 3-ethoxycarbonylpropyl, 3-n-propoxycarbonylpropyl, 3-i-propoxycarbonylpropyl, 4-methoxycarbonylbutyl, 4-ethoxycarbonylbutyl, 2-hydroxyethyl, 3-hydroxypropyl, 4-hydroxybutyl, 5-hydroxypentyl, 6-hydroxyhexyl, 2-dimethylaminoethyl, 2-diethylaminoethyl, 2-di-(n-propyl)aminoethyl, 3-dimethylaminopropyl, 3-diethylaminopropyl, 3-di-(n-propyl)aminopropyl, 4-dimethylaminobutyl, 5-dimethylaminopentyl and 2,2,2-trifluoroethyl.

$R_2$ is chlorine or bromine.

Each of $Y_1$ and $Y_2$ which may be the same or different, includes hydrogen, methyl, ethyl, n-propyl, i-propyl, n-butyl, i-butyl, sec-butyl, n-pentyl, i-pentyl, vinyl, 1-propenyl, 1-butenyl, 1-pentenyl, 1-hexenyl, 1-heptenyl, 1-octenyl, fluorine chlorine, bromine, iodine, hydroxyl, methoxy, ethoxy, n-propoxy, i-propoxy, n- butoxy, i-butoxy, sec-butoxy, n-pentyloxy, n-hexyloxy, n-heptyloxy, n-octyloxy, benzyloxy, phenethyloxy, 3-phenylpropyloxy, 4-phenylbutyloxy, methylthio, ethylthio, n-propylthio, n-butylthio, i-butylthio, carboxy, methoxycarbonyl, ethoxycarbonyl, n-propoxycarbonyl, i-propoxycarbonyl, n-butoxycarbonyl, i-butoxycarbonyl, n-pentyloxycarbonyl, dimethylamino, diethylamino, di-(n-propyl)amino and di-(n-butyl)amino.

$Y_3$ includes methyl, ethyl, n-propyl, i-propyl, n-butyl, i-butyl, sec-butyl, n-pentyl, i-pentyl, vinyl, 1-propenyl, 1-butenyl, 1-pentenyl, 1-hexenyl, 1-heptenhyl, 1-octenyl, fluorine, chlorine, bromine, iodine, hydroxyl, methoxy, ethoxy, n-propoxy, i-propoxy, n-butoxy, i-butoxy, sec-butoxy, n-pentyloxy, n-hexyloxy, n-heptyloxy, n-octyloxy, benzyloxy, phenethyloxy, 3-phenylpropyloxy, 4-phenylbutyloxy, methylthio, ethylthio, n-propylthio, n-butylthio, i-butylthio, carboxy, methoxycarbonyl, ethoxycarbonyl, n-propoxycarbonyl, i-propoxycarbonyl, n-butoxycarbonyl, i-butoxycarbonyl, n-pentyloxycarbonyl, dimethylamino, diethylamino, di-(n-propyl)amino and di-(n-butyl)amino.

Now, a process for the production of the compound of the formula I of the present invention will be described. The compound of the formula I may be prepared by the following reaction scheme 1:

Reaction scheme 1

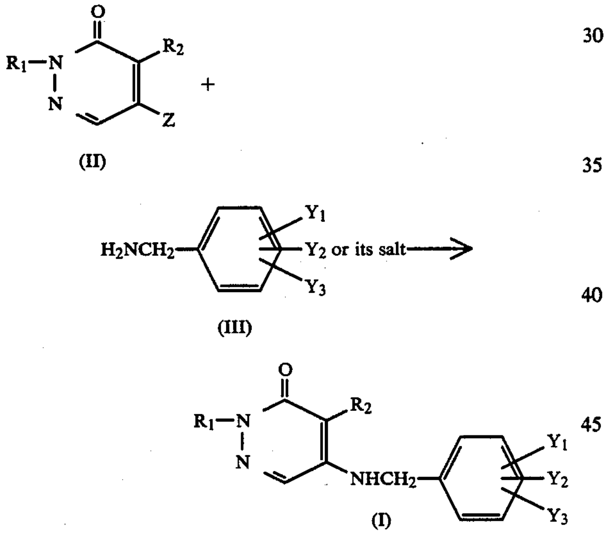

(II) (III) (I)

wherein $R_1$, $R_2$, $Y_1$, $Y_2$ and $Y_3$ are as defined above with respect to the formula I, and Z is chlorine or bromine.

Namely, the compound of the formula I can be prepared by reacting a 3(2H)pyridazinone compound of the formula II, i.e. one of starting materials, with a benzylamine derivative of the formula III or its acid salt in an inert solvent, if necessary, in the presence of a dehydrohalogenating agent.

As the solvent, there may be employed an ether solvent such as diethyl ether, isopropyl ether, tetrahydrofuran or 1,4-dioxane, an amide solvent such as N,N-dimethylformamide, N,N-dimethylacetamide or N-methylpyrrolidone, dimethyl sulfoxide, an alcohol solvent such as methanol, ethanol or 1-propanol, a hydrocarbon solvent such as toluene or benzene, a ketone solvent such as acetone or methyl ethyl ketone, an organic amine solvent such as pyridine or a trialkylamine, or water, or a mixture thereof.

In the above reaction, if $R_2$ is chlorine or bromine, there will be formed, in addition to the compound of the formula I, a compound of the formula IV:

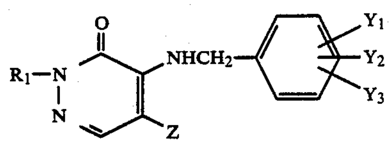

(IV)

wherein $R_1$, Z, $Y_1$, $Y_2$ and $Y_3$ are as defined above with respect to the formula I, which is an isomer of the compound of the formula I with the 5-position substituted by benzylamino, as a by-product. The production rates of the compounds of the formulas I and IV depend upon the polarity of a solvent used. Namely, if a solvent having high polarity, such as water, a lower alcohol, an ether, an amide or dimethyl sulfoxide is used, the production rate of the compound of the formula I tends to be high. On the other hand, if a hydrocarbon solvent such as toluene or benzene is used, the production rate of the compound of the formula IV tends to increase.

Accordingly, in order to efficiently obtain the compound of the formula I, it is preferred to use a solvent having high polarity as mentioned above or to use a solvent mixture of water and an organic solvent, as the case requires.

The compound of the formula I may readily be separated and purified by fractional crystallization or by means of silica gel column chromatography.

As the dehydrohalogenating agent to be used, there may be employed an inorganic base, for instance, potassium carbonate, sodium carbonate or sodium hydrogencarbonate, and an organic base, for instance, a tertiary amine such as N,N-dimethylaniline, N,N-diethylaniline, trimethylamine or triethylamine, pyridine or methylethylpyridine. If necessary, a quarternary amine such as triethylbenzylammonium chloride may be added as an inter-phase transfer catalyst to the reaction system.

The reaction temperature may be within a range of from 10° C. to the boiling point of the solvent used for the reaction.

The molar ratios of the starting materials may optionally be set. However, it is common to use from 1 to 5 mols, preferably from 1 to 3 mols, of the benzylamine derivative of the formula III relative to 1 mol of the pyridazinone derivative of the formula II.

The 3(2H)pyridazinone compound of the formula II, i.e. one of starting materials, may be prepared by known processes as shown by reaction scheme 2 (Advances in Heterocyclic Chemistry, Vol. 9, p. 257 (1968) or by reaction scheme 3 (Chemical Abstract, 62, 2772g).

Reaction scheme 2

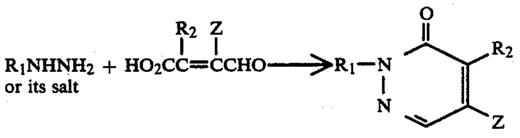

(II)

Reaction scheme 3

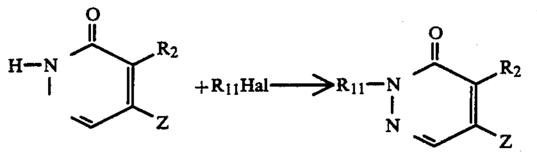

(II')

In reaction schemes 2 and 3, $R_1$, $R_2$ and Z are as defined above with respect to the formula I, and $R_{11}$ is alkyl, benzyl, alkenyl or alkyl substituted by hydroxyl, amino, an ester group or halogen, and Hal is chlorine, bromine or iodine.

Reaction scheme 2 is a reaction for the production of the compounds of the formula II in general by the ring closure reaction of a hydrazine or its acid salt with a mucochloric acid or mucobromic acid. Whereas, reaction scheme 3 is reaction for the production of a compound of the formula II' having a substituent at 2-position among the compounds of the formula II. Namely, it represents an alternative process for the synthesis of the compound of the formula II' by reacting 4,5-(dichloro or bromo)-3-(2H)pyridazinone with a halide of the formula $R_{11}$-Hal (wherein $R_{11}$ and Hal are as defined above). For the production of the compound of the formula II, reaction scheme 2 or 3 may optionally be selected. While it is advantageous to employ reaction scheme 2 from the viewpoint of the yield and operation efficiency, it is usually advantageous to employ reaction scheme 3 when the hydrazine as the starting material is commercially hardly available or difficult to produce economically.

With respect to the other starting material, i.e. a benzylamine of the formula:

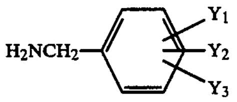

wherein $Y_1$, $Y_2$ and $Y_3$ are as defined above, the one which is hardly available as a commerical product, may be prepared by a known process for the preparation of a benzylamine as shown by reaction scheme 4.

Reaction scheme 4
Processes for the preparation of various benzylamines (A)

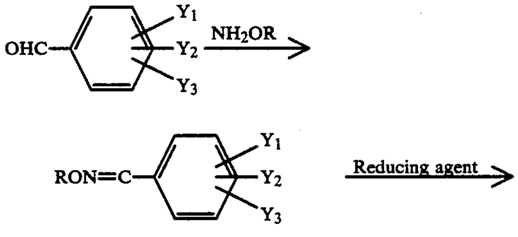

(wherein R is hydrogen or alkyl).

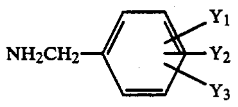

-continued
Reaction scheme 4
Processes for the preparation of various benzylamines (B)

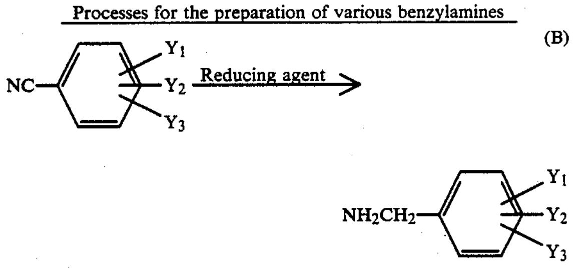

(C)

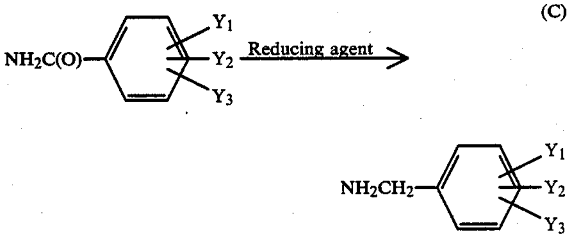

In each of processes A, B and C, the desired benzylamine is prepared by the treatment of the starting material with a reducing agent. The starting material is an intermediate aldoxime prepared by reacting the corresponding aldehyde with hydroxyamine or alkoxyamine in the case of Process A, the corresponding nitrile in the case of Process B, or the corresponding amide in the case of Process C.

Any one of Processes A to C may optionally be employed by using a commercially available product or a starting material derived from such a commercial product. As a method for reduction, there is known (1) a method wherein Raney nickel (nickel-aluminum alloy) is used in the presence of an alkali metal hydroxide such as sodium hydroxide, or (2) a method wherein sodium borohydride is used in the presence of an acid such as acetic acid, trifluoroacetic acid or Lewis acid. A proper method for reduction is selected taking into account the substituents $Y_1$, $Y_2$ and $Y_3$ on the phenyl ring, the economy and the chemical stability. For instance, the reduction method (1) is suitable when the substituents $Y_1$, $Y_2$ and $Y_3$ have a substituent such as alkyl or alkoxy which is durable against a relatively strong reducing agent. Whereas, the reduction method (2) which is a relatively mild reduction method, is suitable when the substituents have a relatively unstable substituent such as a halogen, an olefin, an ester or an amide.

In general, a benzylamine reacts with carbon dioxide in air to form a carbonate. Therefore, for its isolation, it is advantageous, in most cases, to obtain it in the form of an acid salt such as a hydrochloride or a sulfate. A hydrochloride of benzylamine may be subjected by itself to the reaction with 4,5-di-(chloro or bromo)-3(2H)pyridazinone.

The compound of the formula I wherein one, two or three of the substituents $Y_1$, $Y_2$ and $Y_3$ are $-CO_2R_6$ (wherein $R_6$ is $C_1$-$C_5$ alkyl), may readily be prepared by esterifying a compound having the corresponding carboxyl group or its salt with a dialkyl sulfuric acid ester of the formula $(R_6O)_2SO_2$ (wherein $R_6$ is $C_1$-$C_5$ alkyl) in the presence of an acid-binding agent such as sodium hydroxide, potassium hydroxide, potassium or sodium carbonate or bicarbonate, or an organic amine, or with an alcohol of the formula $R_6OH$ (wherein $R_6$ is as defined above) in the presence of an acid catalyst such as sulfuric acid or hydrochloric acid.

In addition to those described in the Examples given hereinafter, the following compounds may be mentioned as the compounds of the present invention. In the following compounds "n" means normal, "i" means iso, "cyc" means cyclo, "Me" means methyl, "Et" means ethyl, "Pr" means propyl, "Bu" means butyl, "Pen" means pentyl, "Hex" means hexyl, "Hep" means heptyl, "Oct" means octyl, and "Ph" means phenyl.

TABLE 1

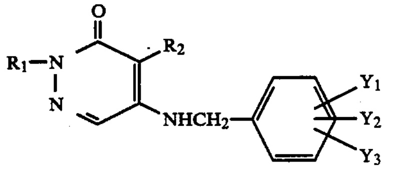

(I)

| $R_1$ | $R_2$ | $Y_1$ | $Y_2$ | $Y_3$ |
|---|---|---|---|---|
| cyc-Pen | Cl | 2-OMe | 4-OMe | H |
| cyc-Pen | Cl | 2-OMe | H | H |
| cyc-Pen | Cl | 4-OMe | H | H |
| $-CH_2CH=CH_2$ | Cl | 4-Me | H | H |
| $-CH_2CH=CH_2$ | Cl | 3-Me | H | H |
| $-CH_2CH=CH_2$ | Cl | 2-Me | H | H |
| $-CH_2CH=CH_2$ | Cl | 2-OMe | H | H |
| $-CH_2CH=CH_2$ | Cl | 4-OMe | H | H |
| Me | Cl | 3-O—n-Bu | H | H |
| Me | Cl | 3-O—n-Bu | 4-OMe | H |
| $-CH_2CH=CH_2$ | Cl | 3-OH | H | H |
| cyc-Pen | Cl | 3-OH | H | H |
| Me | Cl | 2-n-Pr | H | H |
| $-(CH_2)_3OH$ | Cl | 4-CH=CH—n-Pen cis | H | H |
| $-CH_2CH=CH_2$ | Cl | 3-Et | 4-OMe | H |
| $-CH_2CH=CH_2$ | Br | 3-Et | 4-OMe | H |
| $-CH_2CH=CH_2$ | Cl | 2-Me | 4-Me | H |
| $-CH_2CH=CH_2$ | Br | 2-Me | 4-Me | H |
| $-CH_2CH=CH_2$ | Cl | 2-OMe | 4-OMe | H |
| $-CH_2CH=CH_2$ | Br | 2-OMe | 4-OMe | H |
| cyc-Pen | Br | 2-OMe | 4-OMe | H |
| cyc-Pen | Br | 4-OMe | H | H |
| cyc-Pen | Cl | 3-OMe | 4-OMe | H |
| cyc-Pen | Br | 3-OMe | 4-OMe | H |
| H | Cl | 4-CH=CH—Me cis | H | H |
| H | Br | 4-CH=CH—Me cis | H | H |
| H | Cl | 4-CH=CH—Et cis | H | H |
| H | Br | 4-CH=CH—Et cis | H | H |
| H | Cl | 4-CH=CH—n-Pr cis | H | H |
| H | Br | 4-CH=CH—n-Pr cis | H | H |
| H | Cl | 4-CH=CH—n-Pr trans | H | H |
| H | Br | 4-CH=CH—n-Pr trans | H | H |
| H | Cl | 3-OEt | 4-SMe | H |
| H | Br | 3-OEt | 4-SMe | H |
| H | Cl | 3-O—n-Pr | 4-SMe | H |
| H | Br | 3-O—n-Pr | 4-SMe | H |
| H | Cl | 3-O—n-Bu | 4-SMe | H |
| H | Br | 3-O—n-Bu | 4-SMe | H |
| H | Cl | 3-O—n-Pen | 4-SMe | H |
| H | Br | 3-O—n-Pen | 4-SMe | H |
| H | Br | 3-O—n-Hex | 4-SMe | H |
| H | Cl | 3-O—n-Oct | 4-OMe | H |
| H | Br | 3-O—n-Oct | 4-OMe | H |
| H | Cl | 3-O—i-Pr | 4-OMe | H |
| H | Br | 3-O—i-Pr | 4-OMe | H |
| H | Cl | 3-O—sec-Bu | 4-OMe | H |
| H | Cl | 3-O—i-Bu | 4-OMe | H |
| H | Br | 3-O—sec-Bu | 4-OMe | H |
| H | Br | 3-O—i-Bu | 4-OMe | H |
| H | Cl | 3-O—sec-Pen | 4-OMe | H |

TABLE 1-continued

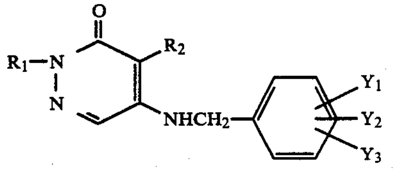

(I)

| $R_1$ | $R_2$ | $Y_1$ | $Y_2$ | $Y_3$ |
|---|---|---|---|---|
| H | Br | 3-O—i-Pen | 4-OMe | H |
| H | Br | 3-O—n-Pr | 4-Cl | H |
| H | Cl | 3-O—n-Pr | 4-Cl | H |
| H | Br | 3-O—n-Bu | 4-Cl | H |
| H | Cl | 3-O—n-Bu | 4-Cl | H |
| H | Br | 3-OEt | 4-OEt | H |
| H | Cl | 3-OEt | 4-OEt | H |
| H | Br | 3-O—n-Pr | 4-OEt | H |

As the manner of administration of the compounds of the present invention, there may be mentioned a non-oral administration by injection (subcutaneous, inravenous, intramuscular or intraperitoneal injection), an ointment, a suppository or an aerosol, or an oral administration in the form of tablets, capsules, granules, pills, sirups, liquids, emulsions or suspensions.

The above pharmacological or veterinary composition contains a compound of the present invention in an amount of from about 0.1 to about 99.5% by weight, preferably from about 0.5 to about 95% by weight, based on the total weight of the composition. To the compound of the present invention or to the composition containing the compound of the present invention, other pharmacologically or veterinarily active compounds may be incorporated. Further, the composition of the present invention may contain a plurality of compounds of the present invention.

The clinical dose of the compound of the present invention varies depending upon the age, the body weight, the sensitivity or the symptom, etc. of the patient. However, the effective daily dose is usually from 0.003 to 1.5 g, preferably from 0.01 to 0.6 g, for an adult. However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as sirups, gum arabic, gelatin, sorbitol, tragacant gum, methyl cellulose or polyvinylpyrrolidone; a disintegrant such as starch, carboxymethyl cellulose or its calcium salt, crystal cellulose powder or polyethylene glycol; a gloss agent such as talc, magnesium or calcium stearate or colloidal silica; or a lubricant such as sodium laurate or glycerol. The injections, solutions, emulsions, suspensions, sirups or aerosols, may be prepared by using a solvent for the active ingredient such as water, ethyl alcohol, isopropyl alcohol, propylene glycole, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl, a cellulose derivative such as methyl cellulose, or a natural rubber such as tragacant gum or gum arabic; or a preservative such as a paraoxy benzoic acid ester, benzalkonium chloride or a salt of sorbic acid. Likewise, the suppositories may be prepared by using e.g. polyethylene glycol, lanolin or cocoa butter.

TEST EXAMPLES

A. Anti-allergic activities

A major constituent of SRS-A which is an important mediator for immediate allergy such as bronchoconstriction in bronchial asthma, has already been found to be leukotriene $C_4$ (hereinafter referred to as $LTC_4$), leukotiene $D_4$ (hereinafter referred to as $LTD_4$) or the like. Accordingly, antagonistic activities against SRS-A can be evaluated by any one of the following test methods:

(1) a method of examining the antagonistic activities against SRS-A obtained from a sensitized guinea-pig, (2) a method of examining the antagonistic activities against $LTC_4$ and (3) a method of examining the antagonistic activities against $LTD_4$.

The present inventors examined the antagonistic activities against SRS-A by using the test methods (1) to (3).

Now, the test methods and the results will be described.

Test methods of anti-allergic activities and the results (i) $LTC_4$ and $LTD_4$ antagonisms in guinea-pig trachea Antagonisms for $LTC_4$ and $LTD_4$ were determined in isolated guinea-pig trachea prepared as spiral strip. Tracheal preparations were suspended under 1 g tension in 10 ml organ baths and they were incubated for 1 hr prior to use. Contractile responses to $LTC_4$ ($2\times10^{-8}$ g/ml) and $LTD_4$ ($2\times10^{-8}$ g/ml) were obtained after the maximal response to histamine ($10^{-4}$M). Test compounds dissolved in 100% dimethyl sulfoxide were added to the organ baths (final concentration of $10^{-5}$ g/ml or $10^{-6}$ g/ml) 5 min prior to $LTC_4$ and $LTD_4$ addition, and then contractile responses to $LTC_4$ and $LTD_4$ were compared with those of control which was obtained from a paired trachea in the absence of test compounds. $LTC_4$- and $LTD_4$-induced contractions were expressed as a percentage of the maximal response to histamine. The antagonism was determined as follows:

Antagonism (%)=(1.0−% contraction in test/% contraction in control)×100

$LTC_4$ antagonisms by test compounds ($10^{-5}$g/ml) are shown in Table 2.

TABLE 2

| Test compound No. | Antagonism (%) |
|---|---|
| 3 | 97 |
| 10 | 29 |
| 13 | 81 |
| FPL-55712 | 100 |

$LTD_4$ antagonisms by test compounds ($10^{-5}$ g/ml) are shown in Table 3.

TABLE 3

| Test compound No. | Antagonism (%) | Test compound No. | Antagonism (%) |
|---|---|---|---|
| 1 | 49 | 17 | 20 |
| 2 | 93 | 18 | 18 |
| 3 | 82 | 19 | 22 |
| 4 | 49 | 20 | 19 |
| 5 | 71 | 21 | 20 |
| 6 | 53 | 22 | 72 |
| 7 | 53 | 23 | 31 |
| 8 | 36 | 24 | 43 |
| 9 | 26 | 25 | 63 |
| 10 | 20 | 26 | 46 |
| 11 | 47 | 27 | 20 |
| 12 | 73 | 28 | 67 |
| 13 | 79 | 29 | 61 |
| 14 | 35 | 30 | 100 |
| 15 | 51 | 31 | 51 |
| 16 | 24 | 32 | 100 |
| | | FPL-55712 | 97 |

(ii) $LTD_4$ antagonism in guinea-pig trachea

Antagonism for $LTD_4$ was determined in isolated guinea-pig trachea prepared as spiral strip. Tracheal preparations were suspended under 1 g tension in 10 ml organ baths containing 5 μmol of indomethacin and they were incubated for 1 hr prior to use. Contractile responses to $LTD_4$ ($2\times10^{-8}$ g/ml) were obtained after the maximal respone to hitamine ($10^{-4}$M). Test compounds dissolved in 100% dimethyl sulfoxide were added to the organ baths (final concentration of $10^{-6}$ g/ml) 30 min prior to $LTD_4$ addition, and then contractile responses to $LTD_4$ were compared with those of control which was obtained from a paired trachea in the absence of test compounds. $LTD_4$-induced contractions were expressed as a percentage of the maximal response to histamine. The antagonism was determined as follows:

Antagonism (%)=(1.0−% contraction in test/% contraction in control)×100

$LTD_4$ antagonisms by test compounds ($10^{-6}$ g/ml) are shown in Table 4. In Table 4, the values with an asterisk "*" were obtained by Test method (i), and others were obtained by Test method (ii).

TABLE 4

| Test compound No. | Antagonism (%) | Test compound No. | Antagonism (%) |
|---|---|---|---|
| 30 | 78* | 44 | 20 |
| 32 | 64* | 45 | 23 |
| 34 | 49* | 46 | 38 |
| 35 | 42* | 47 | 31 |
| 36 | 70* | 48 | 28 |
| 37 | 87* | 49 | 42 |
| 38 | 80* | 50 | 30 |
| 39 | 87* | 52 | 22 |
| 40 | 99 | 53 | 37 |
| 41 | 87 | 54 | 44 |
| 42 | 96 | 55 | 54 |
| 43 | 78 | FPL-55712 | 76*, 94 |

(iii) Effect on anaphylactic bronchoconstriction in passively sensitized guinea-pig Male guinea-pigs (350–450 g) were passively sensitized with intravenous (i.v.) injection of 0.125 ml rabbit anti-EA (egg albumin) serum (Cappel Laboratories) 1 to 2 days preceding the experiment. Antigen-induced anaphylactic bronchoconstrictions were measured by modified method of Konzett and Rossler (Arch. Exp. Path. Pharmak., 195, 71, 1940). Sensitized guinea-pigs were anaesthetized with intraperitoneal injection of urethane (1.5 g/kg). The right jugular vein was cannulated for the administration of the all agents and trachea was cannulated to record total pulmonary resistance.

Guinea-pigs were artificially ventilated by a small animal respirator (Shinano, Model SN-480-7) set at a stroke volume of 4.5 ml and a rate of 50 breaths per min. The change in pulmonary resistance was measured with a pressure transducer (Nihon Kohden, Model TP-602T) connected to a T-tube on the tracheal cannula. The increase in air overflow volume was expresssed as a percentage of the maximum bronchoconstriction obtained by clamping off the trachea. Following surgical preparation, the animals were pretreated with indomethacin (0.2 mg/kg, 10 min), pyrilamine (2 mg/kg, 6 min) and propanolol (0.1 mg/kg, 5 min) prior to the EA challenge (0.1 or 10 mg/kg). All test compounds were administered intraveneously or orally before the EA challenge. Inhibition (%) of bronchoconstriction was determined as follows: Inhibition (%)=(1.0%−maximum bronchoconstriction in test/% maximum bronchoconstriction in control)×100. The maximum bronchoconstriction was btained within 30 min after the EA challenge. The number of test animals was 4 in the i.v. test and 6 in the p.o. test.

(a) The i.v. test: A test compound (2 mg/kg) was suspended or dissolved in 3% Tween 80 and intraveneously administered 1 min prior to the EA challlenge (10 mg/kg). The reaction of the control was 73±9 (means±standard error, n=4), which was suppressed by 27% by 2 mg/kg of FPL-55712 (as identified below).

TABLE 5-(1)

| Test compound No. | Inhibition (%) |
|---|---|
| 3 | 31 |
| 12 | 31 |
| 13 | 19 |
| 25 | 27 |
| FPL-55712 | 27 |

(b) The p.o. test: A test compound was suspended in 5% gum arabic and orally administered 2 hours prior to the EA challenge (0.2 mg/kg). The reaction of the control was 62±6%. No substantial inhibition was observed by the oral administration of FPL-55712 in a dose of 100 mg/kg.

TABLE 5-(2)

| Test compound No. | Dose (mg/kg) | Inhibition (%) |
|---|---|---|
| 30 | 50 | 65 |
| 32 | 50 | 71 |
| 36 | 50 | 68 |
| 38 | 30 | 53 |

The mean inhibition was compared with that of FPL-55712 (Fisons Limited) of the following formula:

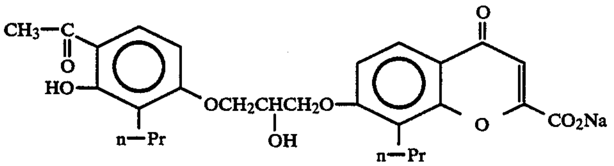

B. Acute toxicity test (i) Test method-(1)

The lethal ratio was determined in ddY strain male mice (4 weeks old) at 7 days after the intraperitoneal injection of test compounds. The results are shown in Table 6.

TABLE 6

| Test compound No. | Dose (mg/kg) | Lethal ratio (Death number/ Experimental number) |
|---|---|---|
| 3 | 200 | 0/2 |
| | 400 | 0/1 |
| 12 | 200 | 0/2 |
| | 400 | 0/1 |
| 13 | 200 | 0/2 |
| | 400 | 0/1 |

(ii) Test method-(2)

The lethal ratio was determined in ddY strain male mice (4 weeks old) at B 7 days after the oral administration of test compounds. The results are shown in Table 7.

TABLE 7

| Test compound No. | Dose (mg/kg) | Lethal ratio (Death number/ Experimental number) |
|---|---|---|
| 38 | 400 | 0/3 |
| | 800 | 0/3 |

From these results, it is evident that the compounds of the present invention produce prominent effects on the angtagonism for SRS-A and its major constituents $LTC_4$ and $LTD_4$ in vitro and in vivo. Therefore, the compounds of the present invention are proved to be useful for prophylactic and therapeutic drugs in SRS-A-induced various allergic diseases, for example bronchial asthma, allergic rhinitics and urticaria.

Now, the present invention will be described in detail with reference to Examples. However, it should be understood that the present invention is by no means restricted by these specific Examples. In Examples or in Reference Examples, the symbols "NMR" and "MS" indicate "nuclear magnetic resonance spectrum" and "mass spectrometry". In the NMR data, only the characteristic absorptions are given. Likewise, in the MS data, only the principal peaks or typical fragment peaks are given.

In this specification, "Me" means a methyl group, "Et" an ethyl group, "Pr" a propyl group, "Bu" a butyl group, "Pen" a pentyl group, "Hex" a hexyl group and "Hep" a heptyl group. Likewise, a "n" indicates normal, "i" indicates iso, "cyc" indicates cyclo and "t" indicates tertiary.

REFERENCE EXAMPLE 1

3,4-Dimethoxybenzylamine hydrochloride

A mixture comprising 24.06 g of 3,4-dimethoxybenzaldehyde, 14.28 g of hydroxylamine sulfate, 7.25 g of sodium hydroxide, 300 ml of methanol and 250 ml of water, was refluxed under stirring for one hour. After cooling, 14.5 g of sodium hydroxide was added and dissolved in the mixture, and then 40 g of Raney nickel (Ni-Al alloy) was gradually added under cooling with ice. After the completion of the addition, the ice bath was removed, and the mixture was continuously stirred at room temperature for one hour. The reaction mixture was filtered, and methanol in the filtrate was distilled off under reduced pressure, and the residue was extracted with diethyl ether. The extract was washed with a saturated sodium chloride aqueous solution, and dried over sodium sulfate, and then the solvent was distilled off to obtain a colorless oily substance.

NMR($CDCl_3$)δ: 6.77 (3H, s), 3.81, 3.80 (each 3H, s), 3.75 (2H, s), 1.58 (2H, s, disappeared upon the addition of $D_2O$)

The residual oily substance was diluted with 100 ml of diethyl ether, and 25 ml of a 1,4-dioxane solution of 6N HCl was added thereto under cooling with ice. The precipitated solid substance was collected by filtration, and washed with ether to obtain 29.36 g of the above identified compound as a colorless powder.

In a similar manner as above, benzylamines having different substituents, i.e. 4-i-propyl, 3-ethoxy, 4-ethoxy, 3-n-propoxy, 3-ethoxy-4-methoxy, 3-n-propoxy-4-methoxy, 3-n-butoxy-4-methoxy, 3-n-pentyloxy-4-methoxy, 3-n-hexyloxy-4-methoxy, 3-n-heptyloxy-4-methoxy, 3-phenethyloxy-4-methoxy and 3,4,5-trimethoxy, and their hydrochlorides were prepared, respectively, from the corresponding benzaldehydes.

REFERENCE EXAMPLE 2

4-Diethylaminobenzylamine hydrochloride

A mixture of 8.80 g of 4-diethylaminobenzaldehyde, 4.59 g of O-methylhydroxylamine hydrochloride, 11.87 g of pyridine and 80 ml of ethanol was refluxed under stirring for one hour. The solvent was distilled off under reduced pressure, and water was added to the residue. The mixture was extracted with benzene. The extract was washed with water (twice) and a saturated sodium chloride aqueous solution, and dried over sodium sulfate, and then the solvent was distilled off to obtain 10.30 g of O-methylaldoxime as a pale yellow oily substance.

NMR($CDCl_3$)δ: 7.87 (1H, s), 7.34, 6.54 (each 2H, ABq), 3.85 (3H, s), 3.33 (4H, q), 1.15 (6H, t)

Into a suspension comprising 7.6 g of sodium borohydride and 200 ml of tetrahydrofuran, a solution obtained by dissolving 22.8 g of trifluoroacetic acid in 10 ml of tetrahydrofuran, was dropwise added over a period of 20 minutes under stirring and cooling with ice. After the completion of the dropwise addition, the ice bath was removed, and the reaction solution was stirred at room temperature for one hour, and then B 10.30 g of the above obtained o-methylaldoxime was added thereto. The reaction was conducted at the same temperature for one hour, and then the mixture was refluxed for two hours. After cooling, water was added to the reaction mixture under cooling with ice to decompose the excess reducing agent. Tetrahydrofuran was distilled off, and the residue thereby obtained was extracted with dichloromethane. The extract was washed with water and a saturated sodium chloride aqueous solution, and dried over sodium sulfate, and then the solvent was distilled off. The, 25 ml of a dioxane solution of 6N HCl was added to the residue under cooling with ice. The mixture was subjected to distillation under reduced pressure. The solid substance thereby obtained was treated with methanol-ether to obtain 11.13 g of the above identified compound as a colorless powder. The NMR spectrum of the free amine is as follows:

NMR($CDCl_3$)δ: 7.06, 6.56 (each 2H, ABq), 3.66 (2H, s), 3.27 (4H, q), 1.55 (2H, s, disappeared upon the addition of $D_2O$), 1.11 (6H, t)

In the same manner as above, benzylamines having various substituents, i.e. 3-hydroxy-4-methoxy, 3-benzyloxy, 3-benzyloxy-4-methoxy, and 4-methylmercapto, and their hydrochlorides, were prepared, respectively, from the corresponding benzaldehydes.

REFERENCE EXAMPLE 3

4-(cis-1-heptenyl)benzylamine hydrochloride

Into a mixture of 617 mg of sodium borohydride and 100 ml of tetrahydrofuran, a mixed solution of 1.86 g of trifluoroacetic acid and 3 ml of tetrahydrofuran, was dropwise added under stirring and cooling with ice. After the completion of the dropwise addition, the ice bath was removed, and the reaction mixture was stirred for one hour. Then, a solution obtained by dissolving 3.09 g of 4-(cis-1-heptenyl)benzonitrile obtained by sujbecting 4-cyanobenzaldehyde and a Wittig reagent formed by treating triphenyl-n-hexylphosphonium bromide in the presence of n-butyl lithium and hexamethyl phosphoric triamide, to a condensation reaction in tetrahydrofuran, in 3 ml of tetrahydrofuran, was dropwise added to the reaction mixture, and stirred at room temperature for 3 hours. Ice pieces were added to decompose the excess reducing agent. Then, the solvent was distilled off from the reaction mixture, and the residue was extracted with benzene. The extract was washed with water and a saturated sodium chloride aqueous solution and dried over sodium sulfate, and then the solvent was distilled off to obtain a pale yellow oily substance. The product was dissolved in 80 ml of ethyl ether, and 3 ml of a 1,4-dioxane solution of 6N HCl was added under cooling with ice. The precipitated solid was collected by filtration and washed with ethyl ether to obtain 3.47 g of the above identified compound as a pale yellow solid substance. The NMR spectrum of the free amine is as follows.

NMR($CDCl_3$)δ: 7.17 (4H, s), 4.33 (1H, d, J=10.8 Hz), 3.78 (2H, s)

REFERENCE EXAMPLE 4

4-Chlorobenzylamine hydrochloride

Into a mixture comprising 7.30 g of sodium borohydride, 6.00 g of 4-chlorobenzamide and 100 ml of 1,4-dioxane, a mixed solution of 11.58 g of acetic acid and 30 ml of 1,4-dioxane, was dropwise added under stirring and cooling with ice over a period of 30 minutes. After the dropwise addition, the reaction mixture was refluxed under stirring for two hours. After cooling, ice pieces were gradually added to decompose the excess reducing agent, and the solvent was distilled off under reduced pressure. Then, the residue was extracted with chloroform. The extract was washed with a saturated sodium chloride aqueous solution, and dried over sodium sulfate, and then the solvent was distilled off to a concentration of about 80 ml. The concentrated solution was cooled with ice, and 10 ml of a dioxane solution of 6N HCl was dropwise added thereto. The precipitated solid substance was treated with methanol-ether to obtain 3.16 g of the above identified compound as a colorless powder. The NMR spectrum of the free amine is as follows:

NMR($CDCl_3$)δ: 7.38 (4H, s), 4.16 (2H, s), 1.55(2H, s, disappeared upon the addition of $D_2O$)

REFERENCE EXAMPLE 5

4,5-Dichloro-2-allyl-3(2H)pyridazinone

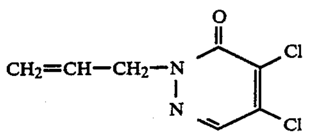

Into a mixture comprising 16.4 g of 4,5-dichloro-3(2H)pyridazinone, 14.5 g of allyl bromide and 60 ml of dimethylformamide, 4.3 g of sodium hydride (55% mineral oil suspension) was gradually added at a temperature of from 15° to 20 C., and stirred at a temperature of from 20° to 25° C. for about 2 hours. The reaction mixture was cooled, then poured into 200 ml of cool water, and extracted with hexane-benzene (5:1, v/v). The organic layer was dried, and the solvent was distilled off. The crude crystals obtained were recrystallized from n-hexane to obtain 10.3 g of the above identified compound. The melting point was 45° C.

REFERENCE EXAMPLE 6

4,5-Dichloro-2-benzyl-3(2H)pyridazinone

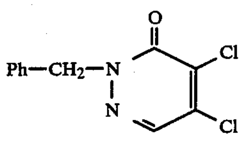

In the same manner as in Reference Example 5, 7.5 g of the above identified compound was prepared from 8.2 g of 4,5-dichloro-3(2H)pyridazinone, 6.4 g of benzylchloride, 2.2 g of sodium hydride and 40 ml of dimethylformamide.

The melting point was 86° C. (as recrystallized from n-hexane).

REFERENCE EXAMPLE 7

4,5-Dichloro-2-cyclopentyl-3(2H)pyridazinone

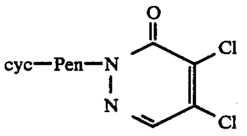

In the same manner as in Reference Example 5, 4.5 g of the above identified compound was obtained from 16.5 g of 4,5-dichloro-3(2H)pyridazinone, 22.8 g of cyclopentyl bromide, 4.3 g of sodium hydride and 60 ml of dimethylformamide.

The melting point was from 56° to 57° C. (as recrystallized from methanol:water=1:10, v/v).

REFERENCE EXAMPLE 8

4,5-Dichloro-2-(2,2,2-trifluoroethyl)-3(2H) pyridazinone

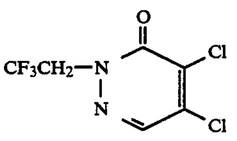

In the same manner as in Reference Example 5, 15.3 g of the above identified compound was prepared from 16.5 g of 4,5-dichloro-3(2H)pyridazinone, 17.9 g of 2,2,2-trifluoroethylbromide, 4.3 g of sodium hydride and 60 ml of dimethylformamide.

The melting point was 62° C. (as recrystallized from n-hexane).

REFERENCE EXAMPLE 9

4,5-Dichloro-2-carboxymethyl-3(2H)pyridazinone

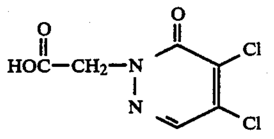

A mixture comprising 12.4 g of 4,5-dichloro-3(2H)pyridazinone, 14.6 g of iodeacetic acid , 20.7 g of potassium carbonate and 100 ml of dimethylformamide, was stirred at 50° C. for 4 hours.

After the completion of the reaction, the solvent was distilled off, and 60 ml of a 10% sodium hydroxide aqueous solution and 100 ml of benzene were added. The mixture was vigorously shaked. The benzene layer was removed, and the aqueous layer was acidified with 10% hydrochloric acid, and then extracted with 100 ml of ethyl acetate and dried.

The solvent was distilled off, and the crude crystals thus obtained were recrystallized (ethyl acetate:ethyl ether:petroleum benzine=1:1:1, v/v) to obtain 3.26 g of the above identified compound.

The melting point was from 175° to 177° C.

REFERENCE EXAMPLE 10

4,5-Dichloro-2-(2-hydroxyethyl)-3(2H)pyridazinone

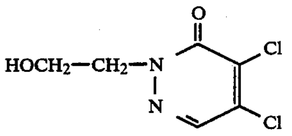

A mixture comprising 16.5 g of 4,5-dichloro-3(2H)pyridazinone, 15 g of 2-bromoethanol, 16.5 g of potassium carbonate, 1.5 g of sodium iodide and 60 ml of dimethylformamide, was stirred at 60° C. for 4 hours. The solvent was ditilled off, and 80 ml of ethyl acetate and 80 ml of water were added thereto. The mixture was vigorously shaked, and the ethyl acetate layer was dried over anhydrous sodium sulfate. The solvent was distilled off, and the oily substance thus obtained was purified by silica gel column chromatography (developer: ethyl acetate) to obtain 8.7 g of the above identified compound as a pale yellow oily substance.

REFERENCE EXAMPLE 11

4,5-Dichloro-2-(3-hydroxypropyl)-3(2H)pyridazinone

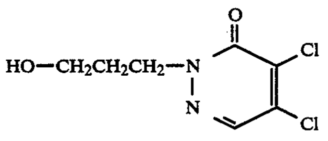

In the same manner as in Reference Example 10, a mixture comprising 16.5 g of 4,5-dichloro-3(2H)pyridazinone, 16.7 g of 3-bromo-1-propanol, 16.6 g of potassium carbonate, 1.5 g of sodium iodide and 70 ml of dimethylformamide, was reacted, and the oily substance thus obtained was purified by silica gel column chromatography (developer: benzene:ethyl acetate=1:1, v/v) to obtain 13.7 g of the above identified compound as a pale yellow oily substance.

REFERENCE EXAMPLE 12

4,5-Dichloro-2-(2,2-dimethylaminoethyl)-3(2H) pyridazinone

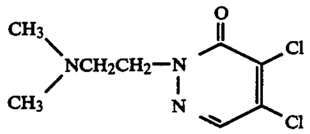

In the same manner as in Reference Example 10, a mixture comprising 41.0 g of 4,5-dichloro-3(2H)pyridazinone, 40.4 g of 2,2-dimethylaminoethyl chloride, 64.5 g of potassium carbonate, 42.1 g of sodium iodide and 80 ml of dimethylformamide, was reacted, and the oily substance thus obtained was purified by silica gel column chromatography (developer: chloroform:methanol=5:1, v/v) to obtain 7.72 g of the above identified compound as a pale yellow oily substance.

REFERENCE EXAMPLE 13

4,5-Dichloro-2-{2-(t-butoxycarbonyl)ethyl}-3(2H) pyridazinone

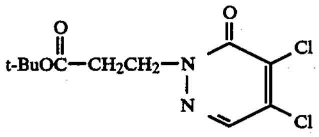

In the same manner as in Reference Example 10, a mixture comprising 19.3 g of 4,5-dichloro-3(2H) pyridazinone, 29.4 g of 2-(t-butoxycarbonyl)ethylbromide, 19.3 g of potassium carbonate, 1.75 g of sodium iodide and 60 ml of dimethylformamide, was reacted, and the oily substance thus obtained was purified by silica gel column chromatography (developer: benzene:ethyl acetate=10:1, v/v) to obtain 8.1 g of the above identified compound as a pale yellow oily substance.

EXAMPLE 1

4-Chloro-5-(3-methoxybenzylamino)-2-cyclopentyl-3(2H)pyridazinone (Compound No. 3)

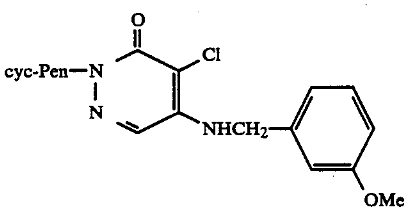

A mixture comprising 0.75 g of 3-methoxybenzylamine, 0.5 g of 4,5-dichloro-2-cyclopentyl-3(2H)pyridazinone, 0.4 g of potassium carbonate, 5 ml of 1,4-dioxane and 15 ml of water, were refluxed under stirring for 7 hours. The solvent was distilled off under reduced pressure, and water was added to the residue. The mixture was extracted with ethyl acetate. The extract was sequentially washed with 2% dilute hydrochloric acid, water and a saturated sodium chloride aqueous solution, and dried over sodium sulfate. Then, the solvent was distilled off to obtain a pale yellow oily substance. This product was crystallized from diethyl ether-n-hexane to obtain 250 mg of the above identified compound as colorless crystals having a melting point of from 113° to 115° C.

NMR($CDCl_3$)δ: 7.54 (1H, s), 4.53, 4.43 (total 2H, each s), 3.77 (3H, s), 2.24–1.52 (9H, m)

EXAMPLE 2

4-Chloro-5-(3,4-dimethoxybenzylamino)-2-(2-N,N-dimethylaminoethyl)-3(2H)pyridazinone (Compound No. 8)

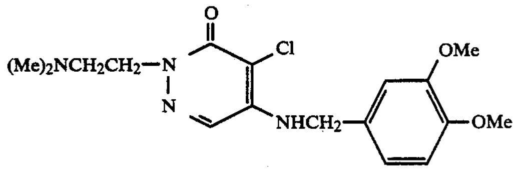

A mixture comprising 500 mg of 4,5-dichloro-2-(2-N,N-dimethylaminoethyl)-3(2H)pyridazinone, 1.29 g of 3,4-dimethoxybenzylamine hydrochloride, 1.18 g of potassium carbonate, 6 ml of 1,4-dioxane and 18 ml of water, was refluxed under stirring for 7 hours. 1,4-dioxane was distilled off under reduced pressure, and the residue was extracted with chloroform. The chloroform layer was dried over sodium sulfate, and the solvent was distilled off. The residue was purified by silica gel column chromatography (developer: chloroform:methanol=5:1), and further crystallized from acetone-n-hexane to obtain 270 mg of the above identified compound as yellow crystals having a melting point of from 180° to 182° C.

NMR($CDCl_3$)δ: 7.55 (1H, s), 6.82 (3H, s), 5.04 (1H, brs), 4.47, 4.37 (total 2H, each s), 4.21 (2H, t), B 3.84 (6H, s), 2.66 (2H, t), 2.25 (6H, s)

Mass (m/e): 330 ($M^+$-HCl), 296, 150, 71 (100%)

EXAMPLE 3

4-Chloro-5-(3-n-pentyloxy-4-methoxybenzylamino)-2-{2-(t-butyloxycarbonyl)ethyl}-3(2H)pyridazinone (Compound No. 16)

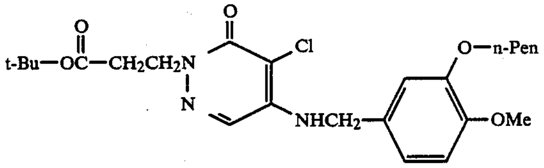

A mixture comprising 1.43 g of 4,5-dichloro-2-{2-(t-butyloxycarbonyl)ethyl}-3(2H)pyridazinone, 3.8 g of 3-n-pentyloxy-4-methoxybenzylamine hydrochloride, 2.69 g of potassium carbonate, 25 ml of 1,4-dioxane and 75 ml of water, was refluxed under stirring for 8 hours. Then, 1,4-dioxane was distilled off under reduced pressure, and the residue was extracted with ethyl acetate. The extract was sequentially washed with dilute hydrochloric acid and water, and dried over sodium sulfate. Then, the solvent was distilled off, and the residue thus obtained was purified by silica gel column chromatography (developer: benzene:ethyl acetate=2:1) to obtain 1.56 g of the above identified compound as a pale yellow viscous substance.

NMR($CDCl_3$)δ: 7.53 (1H, s), 6.82 (3H, s), 5.18 (1H, brs), 4.48, 4.38 (total 2H, each s), 4.30–3.80 (4H, m), 3.83 (3H, s), 2.70 (2H, s), 2.00–1.10 (6H, m), 1.40 (9H, s), 0.93 (3H, t)

Mass (m/e): 479 ($M^+$), 388, 207 (100%), 137

EXAMPLE 4

4-Chloro-5-(3,4-dimethoxybenzylamino)-2-(carboxymethyl)-3(2H)pyridazinone (Compound No. 10)

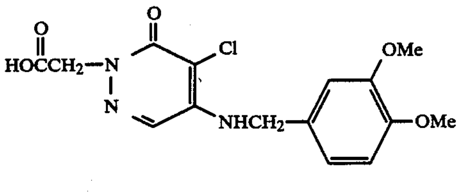

a mixture comprising 178 mg of 4,5-dichloro-2-carboxymethyl-3(2H)pyridazinone, 1.018 g of 3,4-dimethoxy benzylamine hydrochloride, 1.11 g of potassium carbonate, 2 ml of 1,4-dioxane and 20 ml of water, was refluxed under stirring for 17 hours. The majority of 1,4-dioxane was distilled under reduced pressure, and dilute hydrochloric acid was added to the residue to bring the pH to about 2.0. Then, the residue was extracted with ethyl acetate. The extract was sequentially washed with water and a saturated sodium chloride aqueous solution, and dried over sodium sulfate. Then, the solvent was distilled off to obtain a slightly yellow oily substance. The residue was subjected to silica gel column chromatography by using chloroform-methanol (8:1, v/v) as the developer. The solvent was distilled off to obtain a slightly yellow viscous oily substance, which was crystallized from methanol-diethyl ether to obtain 119 mg of the above identified compound as colorless crystals having a melting point of from 168° to 171° C.

NMR($CDCl_3$+DMSO-$d_6$): 7.54 (1H, s), 6.79 (3H, s), 5.9–5.4 (1H, m), 4.74 (2H, s), 4.49, 4.39 (total 2H, each s), 3.82 (6H, s) Mass (m/e): 353 ($M^+$), 318, 151 (100%)

EXAMPLE 5

4-Chloro-5-(3,4-dimethoxybenzylamino)-2-(2-N,N-dimethylaminoethyl)-3(2H)pyridazinone hydrochloride (Compound No. 9)

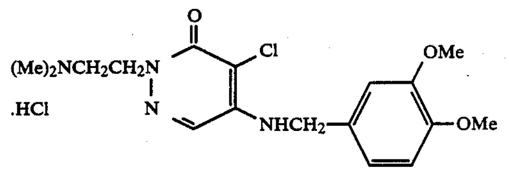

To a mixed solution comprising 150 mg of 4-chloro-5-(3,4-dimethoxybenzylamino)-2-(2-N,N-dimethylaminoethyl)-3(2H)pyridazinone obtained in Example 2 and 10 ml of chloroform, 2 ml of a 1,4-dioxane solution of 6N HCl was added under cooling with ice. The mixture was left to stand at room temperature for 2 hours, and then the solvent was distilled off under reduced pressure. The residue thus obtained was dissolved in 5 ml of water and naturally filtered. The filtrate was freeze-dried to obtain 120 mg of the above identified compound as hygroscopic yellow crystals.

EXAMPLE 6

4-Bromo-5-(3-n-pentyloxy-4-methoxybenzylamino)-3(2H)-pyridazinone (Compound No. 39)

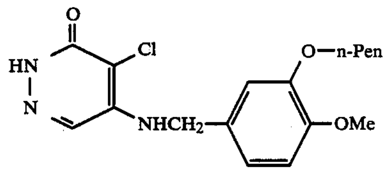

A mixture comprising 1.52 g of 4,5-dibromo-3(2H) pyridazinone, 4.01 g of 3-n-pentyloxy-4-methoxybenzylamine and 60 ml of ethanol was refluxed under stirring for 7.5 hours. Then, ethanol was distilled off under reduced pressure, and the residue thus obtained was extracted with ethyl acetate. The extract was sequentially washed with dilute hydrochloric acid and water, and dried over sodium sulfate. Then, the solvent was distilled off, and the residue thus obtained was crystallized from ethyl acetate-diethyl ether to obtain 1.42 g of the above identified compound as pale yellow crystals having a melting point of from 148° to 150° C.

NMR($CDCl_3$)δ: 7.51 (1H, s), 6.82 (3H, s), 5.28 (1H, brs), 4.51, 4.41 (total 2H, each s), 3.97 (2H, t), 3.84 (3H, s), 2.05–1.05 (6H, m), 0.96 (3H, t)

Mass (m/e): 395 ($M^+$), 316 (100%), 207, 137

The compounds prepared in accordance with the above Examples are shown in Table 8. In the right hand end column in the Table, the numbers of the Examples in accordance with which the respective compounds were prepared, are indicated.

TABLE 8

Synthesis of

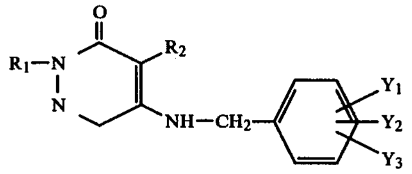

| Compound No. | $R_1$ | $R_2$ | $Y_1$ | $Y_2$ | $Y_3$ | mp(°C.) | NMR ($CDCl_3$)δ | Example No. |
|---|---|---|---|---|---|---|---|---|
| 1 | Me | Cl | 4-i-Pr | H | H | 161–161.5 | 7.46 (1H, s), 4.51, 4.41 (total 2H, each s), 3.68 (3H, s), 1.25 (6H, d) | 1 |
| 2 | $-CH_2CH{=}CH_2$ | Cl | 4-Cl | H | H | 142–142.5 | 7.47 (1H, s), 6.26–5.56 (1H, m), 4.70 (2H, d), 4.57, 4.47 (total 2H, each s) | 1 |
| 3 | cyc-Pen | Cl | 3-OMe | H | H | 113–115 | See Example 1 | 1 |
| 4 | Me | Cl | 3-O—Et | H | H | 138.5 | 7.47 (1H, s), 4.54, 4.44 (total 2H, each s), 3.72 (3H, s), 1.41 (3H, t) | 1 |
| 5 | Me | Cl | 3-O—n-Pr | H | H | 111.5 | 7.49 (1H, s), 4.56, 4.46 (total 2H, each s), 3.74 (3H, s), 1.08 (3H, t) | 1 |
| 6 | $-CH_2CH{=}CH_2$ | Cl | 3-OMe | 4-OMe | H | 141–142.5 | 7.57 (1H, s), 6.16–5.65 (1H, m), 4.71 (2H, d), 4.51, 4.41 (total 2H, each s), 3.86 (6H, s) | 1 |
| 7 | Me | Cl | 3-$OCH_2$Ph | H | H | 119–120 | 7.45 (1H, s), 7.37 (5H, s), 4.54 4.44 (total 2H, each s), 3.72 (3H, s) | 1 |
| 8 | $-(CH_2)_2N(Me)_2$ | Cl | 3-OMe | 4-OMe | H | 180–182 | See Example 2 | 2 |
| 9 | $-(CH_2)_2N(Me)_2$.HCl | Cl | 3-OMe | 4-OMe | H | Hygroscopie powder | See Example 5 | 5 |
| 10 | $-CH_2CO_2H$ | Cl | 3-OMe | 4-OMe | H | 168–171 | See Example 4 | 4 |
| 11 | $-CH_2CF_3$ | Cl | 3-OMe | 4-OMe | H | 168–169.5 | 7.62 (1H, s), 4.72 (2H, d, J=8.4Hz), 4.52, 4.44 (total 2H), 3.87 (6H, s) | 1 |
| 12 | Me | Cl | 3-O—n-Pr | 4-OMe | H | 156–156.5 | 7.44 (1H, s), 4.45, 4.35 (total 2H, each s), 3.81 (3H, s), 3.69 (3H, s), 1.02 (3H, t) | 1 |
| 13 | Me | Cl | 3-OEt | 4-OMe | H | 157.5–158 | 7.54 (1H, s), 4.50, 4.40 (total 2H, each s), 3.86 (3H, s), 3.74 (3H, s), 1.45 (3H, t) | 1 |
| 14 | $-(CH_2)_2OH$ | Cl | 3-O—n-Pen | 4-OMe | H | Viscous oily substance | 7.59 (1H, s), 4.50, 4.40 (total 2H, each s), 3.83 (3H, s), 0.93 (3H, t) | 1 |
| 15 | $-(CH_2)_3OH$ | Cl | 3-O—n-Pen | 4-OMe | H | 105 | 7.60 (1H, s), 4.53, 4.43 (total 2H, each s), 3.83 (3H, s), 0.92 (3H, t) | 1 |
| 16 | $-(CH_2)_2CO_2$t-Bu | Cl | 3-O—n-Pen | 4-OMe | H | Viscous oily substance | See Example 3 | 3 |
| 17 | $-CH_2CO_2H$ | Cl | 3-O—n-Pen | 4-OMe | H | 174–175 | 7.55 (1H, s), 3.78 (3H, s), 0.91 (3H, t) | 4 |
| 18 | $-(CH_2)_2CO_2H$ | Cl | 3-O—n-Pen | 4-OMe | H | 161–163 | See Example 6 | 6 |
| 19 | Me | Cl | 3-OMe | 4-OMe | 5-OMe | 145.5 | 7.51 (1H, s), 4.52, 4.42 (total 2H, each s), 3.82 (9H, s), 3.72 (3H, s) | 1 |
| 20 | $-(CH_2)_3OH$ | Cl | 3-OMe | 4-OMe | 5-OMe | 127–129 | 7.64 (1H, s), 4.54, 4.44 (total 2H, each s), 3.84 (9H, s), 3.54 (2H, t) | 1 |

TABLE 8-continued

| | | | | | | | | |
|---|---|---|---|---|---|---|---|---|
| | | | | Synthesis of | | | | |
| 21 | $-(CH_2)_2N(Me)_2$ | Cl | 3-OH | 4-OMe | H | Semi-solid substance | 7.52 (1H, s), 4.44, 4.34 (total 2H, each s), 3.86 (3H, s), 2.39 (6H, s) | 2 |
| 22 | $-CH_2CH{=}CH_2$ | Cl | 4-SMe | H | H | 148 | 7.52 (1H, s), 4.80 (2H, d), 4.53, 4.43 (total 2H, each s), 2.47 (3H, s) | 1 |
| 23 | $-CH_2CO_2H$ | Cl | 4-CH=CH—n-Pen(cis) | H | H | Semi-solid substance | 7.50 (1H, s), 6.30 (1H, d, J=11.4Hz) 5.20-5.85 (3H, m), 4.41 (2H, broads), 2.0-2.8 (2H, m) | 4 |
| 24 | Me | Cl | $4\text{-}CO_2$—n-Bu | H | H | 120-122 | 7.47 (1H, s), 4.70, 4.60 (total 2H, each s), 3.75 (3H, s), 1.00 (3H, t) | 1 |
| 25 | H | Cl | $4\text{-}N(Me)_2$ | H | H | 280 (decomposed) | ($CDCl_3$ + DMSO—$d_6$): 7.52 (1H, s), 4.46, 4.35 (total 2H, each s), 2.87 (6H, s) | 2 |
| 26 | Me | Cl | $4\text{-}N(Et)_2$ | H | H | 158 | 7.50(1H, s), 4.37, 4.27 (total 2H, eash s), 3.65 (3H, s), 1.13 (6H, t) | 2 |
| 27 | Me | Cl | $4\text{-}CO_2H$ | H | H | 275 | (DMSO—$d_6$): 7.68 (1H, s), 4.71, 4.61 (total 2H, each s), 3.64 (3H, s) | 1 |
| Compound No. | $R_1$ | $R_2$ | $Y_1$ | $Y_2$ | $Y_3$ | mp(°C.) | Ms (m/e) | Example No. |
| 28 | H | Cl | 4-OMe | H | H | 215-216 | 265 ($M^+$), 121 (100%) | 6 |
| 29 | H | Br | 3-O—n-Pr | H | H | 164-166.5 | 258 ($M^+$—Br, 100%) | 6 |
| 30 | H | Br | 3-O—n-Pr | 4-OMe | H | 169-171 | 367 ($M^+$), 179 (100%) | 6 |
| 31 | H | Cl | 3-O—n-Pr | H | H | 177-179 | 293 ($M^+$), 258 (100%) | 6 |
| 32 | H | Cl | 3-O—n-Pr | 4-OMe | H | 153-154 | 323 ($M^+$), 179 (100%) | 6 |
| 33 | H | Cl | 4-OEt | H | H | 165-167 | 279 ($M^+$), 135 (100%) | 6 |
| 34 | H | Cl | 3-O—n-Bu | 4-OMe | H | 206-207 | 337 ($M^+$), 193 (100%) | 6 |
| 35 | H | Cl | 3-OEt | 4-OMe | H | 173-174 | 309 ($M^+$), 165 (100%) | 6 |
| 36 | H | Br | 3-OEt | 4-OMe | H | 170-174 | 353 ($M^+$), 165 (100%) | 6 |
| 37 | H | Cl | 3-O—n-Pen | 4-OMe | H | 156-158 | 351 ($M^+$), 207 (100%) | 6 |
| 38 | H | Br | 3-O—n-Bu | 4-OMe | H | 194-197 | 381 ($M^+$), 193 (100%) | 6 |
| 39 | H | Br | 3-O—n-Pen | 4-OMe | H | 148-150 | See Example 7 | 6 |
| 40 | H | Cl | 3-O—n-Hex | 4-OMe | H | 113-117 | 365 ($M^+$), 221 (100%) | 6 |
| 41 | H | Br | 3-O—n-Hex | 4-OMe | H | 126-127.5 | 409 ($M^+$), 221 (100%) | 6 |
| 42 | H | Cl | 3-O—n-Hep | 4-OMe | H | 97-99 | 379 ($M^+$), 235 (100%) | 6 |
| 43 | H | Br | 3-O—n-Hep | 4-OMe | H | 124-125 | 355 ($M^+$), 121 (100%) | 6 |
| 44 | Ph | Cl | 4-OMe | H | H | 134.5-136 | 341 ($M^+$), 121 (100%) | 1 |
| 45 | $PhCH_2$ | Cl | 4-OMe | H | H | 130-133 | 355 ($M^+$), 121 (100%) | 1 |
| 46 | Cyc-Pen | Cl | 3-OEt | 4-OMe | H | 155.5-157 | 377 ($M^+$), 165 (100%) | 1 |
| 47 | $-CH_2CH{=}CH_2$ | Cl | 3-O—n-Pr | 4-OMe | H | 107 | 363 ($M^+$), 179 (100%) | 1 |
| 48 | $-CH_2CH{=}CH_2$ | Cl | 3-OEt | 4-OMe | H | 106-107.5 | 349 ($M^+$), 165 (100%) | 1 |
| 49 | Ph | Cl | 3-OEt | 4-OMe | H | 163-165 | 385 ($M^+$), 165 (100%) | 1 |
| 50 | $PhCH_2$ | Cl | 3-OEt | H | H | 135-137 | 369 ($M^+$), 106 (100%) | 1 |
| 51 | $-CH_2CH{=}CH_2$ | Cl | 3-OMe | H | H | 103-104 | 305 ($M^+$), 270 (100%) | 1 |
| 52 | H | Cl | 2-Me | 4-Me | H | 255-258 | 263 ($M^+$), 119 (100%) | 6 |
| 53 | H | Br | 2-Me | 4-Me | H | 245-252 | 307 ($M^+$), 119 (100%) | 6 |
| 54 | H | Cl | $3\text{-}OCH_2Ph$ | 4-OMe | H | 190-191 | 371 ($M^+$), 91 (100%) | 6 |
| 55 | H | Br | $2\text{-}OCH_2Ph$ | 4-OMe | H | 194-197 | 415 ($M^+$), 91 (100%) | 6 |
| 56 | H | Cl | $3\text{-}OCH_2CH_2Ph$ | 4-OMe | H | 190-191 | 385 ($M^+$), 105 (100%) | 6 |
| 57 | H | Br | $3\text{-}OCH_2CH_2Ph$ | 4-OMe | H | 154-155 | 429 ($M^+$), 105 (100%) | 6 |
| 58 | H | Cl | 3-OMe | 4-OMe | H | 190-192 | 295 ($M^+$), 151 (100%) | 6 |
| 59 | H | Br | 3-OMe | 4-OMe | H | 198-200 | 339 ($M^+$), 151 (100%) | 6 |

Now, Formulation Examples of the compounds of the formula I will be given.

| FORMULATION EXAMPLES 1 and 2 (Tablets) | |
|---|---|
| Compound No. 2 (Formulation Example 1) or Compound No. 38 (Formulation Example 2) | 10 g |
| Lactose | 20 g |
| Starch | 4 g |
| Starch for paste | 1 g |
| Magnesium stearate | 100 mg |
| Carboxymethyl cellulose calcium | 7 g |
| Total | 42.1 g |

The above components were mixed in a usual manner, and formulated into sugar-coated tablets each containing 50 mg of an active ingredient.

| FORMULATION EXAMPLES 3 and 4 (Capsules) | |
|---|---|
| Compound No. 3 (Formulation Example 3) or Compound No. 32 (Formulation Example 4) | 10 g |
| Lactose | 20 g |
| Crystal cellulose powder | 10 g |
| Magnesium stearate | 1 g |
| Total | 41 g |

The above components were mixed in a usual manner, and filled into a gelatin capsule to obtain capsules each containing 50 mg of an active ingredient.

| FORMULATION EXAMPLES 5 and 6 (Soft capsules) | |
|---|---|
| Compound No. 12 (Formulation Example 5) or Compound No. 39 (Formulation Example 6) | 10 g |
| Corn oil | 35 g |
| Total | 45 g |

The above components were mixed in a usual manner to obtain soft capsules.

| FORMULATION EXAMPLES 7 and 8 (Ointment) | |
|---|---|
| Compound No. 13 (Formulation Example 7) or Compound No. 41 (Formulation Example 8) | 1.0 g |
| Olieve oil | 20 g |
| White vaseline | 79 g |
| Total | 100 g |

The above components were mixed in a usual manner to obtain 1% ointment.

| FORMULATION EXAMPLES 9 and 10 (Aerosol suspension) | | |
|---|---|---|
| (A) | Compound No. 2 (Formulation Example 9) or Compound No. 37 (Formulation Example 10) | 0.25 (%) |
| | Isopropyl myristate | 0.10 |
| | Ethanol | 26.40 |
| (B) | A 60-40% mixture of 1,2-dichlorotetrafluoroethane and 1-chloropentafluoroethane | 73.25 |

The above composition (A) was mixed. The solution mixture thereby obtained was charged in a container equipped with a valve, and the propellant (B) was injected from a valve nozzle to a gauge pressure of from about 2.46 to 2.81 kg/cm$^2$ to obtain an aerosol suspension.

We claim:

1. A 3(2H)pyridazinone of the formula:

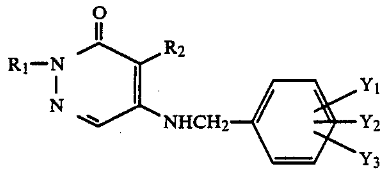

wherein $R_1$ is hydrogen; methyl; $C_3$-$C_6$ alkenyl; $C_5$ or $C_6$ cycloalkyl; benzyl; phenyl; $-(CH_2)_mCO_2R_3$, wherein $R_3$is hydrogen or $C_1$-$C_5$ alkyl, and m is an integer of from 1 to 4; $-(CH_2)_nA$, wherein A is $-OH$ or $-N(R_4)_2$, wherein $R_4$ is $C_1$-$C_3$ alkyl, and n is an integer of from 2 to 6; or $-CH_2CF_3$;

$R_2$ is chlorine or bromine;

each of $Y_1$ and $Y_2$ which may be the same or different, is hydrogen; $C_1$-$C_5$ alkyl; $C_2$-$C_8$ alkenyl; halogen; $-OR_5$, wherein $R_5$ is hydrogen, $C_1$-$C_8$ alkyl or $-(CH_2)_q$-phenyl, wherein q is an integer of from 1 to 4; $-CO_2R_6$, wherein $R_6$ is hydrogen or $C_1$-$C_5$ alkyl; $-N(R_7)_2$, wherein $R_7$ is $C_1$-$C_4$ alkyl; or $-SR_8$, wherein $R_8$ is $C_1$-$C_4$ alkyl; and $Y_3$ is halogen;

or a pharmaceutically acceptable salt thereof.

2. A 3(2H)pyridazinone of the formula:

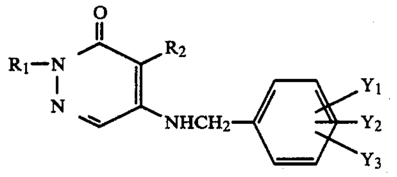

wherein $R_1$ is hydrogen; methyl; $C_3$-$C_6$alkenyl; $C_5$ or $C_6$ cycloalkyl; benzyl; phenyl; $-(CH_2)_mCO_2R_3$, wherein $R_3$ is hydrogen or $C_1$-$C_5$ alkyl, and m is an integer of from 1 to 4; $-(CH_2)_nA$, wherein A is $-OH$ or $-N(R_4)_2$, wherein $R_4$ is $C_1$-$C_3$ alkyl, and n is an integer of from 2 to 6; or $-CH_2CF_3$;

$R_2$ is chlorine or bromine;

each of $Y_1$ and $Y_2$ which may be the same or different, is hydrogen; $C_1$-$C_5$ alkyl; $C_2$-$C_8$ alkenyl; halogen; $-OR_5$, wherein $R_5$ is hydrogen, $C_1$-$C_8$ alkyl or $-(CH_2)_q$-phenyl, wherein q is an integer of from 1 to 4; $-CO_2R_6$, wherein $R_6$ is hydrogen or $C_1$-$C_5$ alkyl; $-N(R_7)_2$, wherein $R_7$ is $C_1$-$C_4$ alkyl; or $-SR_8$, wherein $R_8$ is $C_1$-$C_4$ alkyl; and $Y_3$ is $-OR_5$, wherein $R_5$ is as defined above;

or a pharmaceutically acceptable salt thereof.

3. A 3(2H)pyridazinone of the formula:

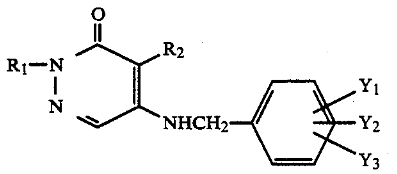

wherein $R_1$ is hydrogen; methyl; $C_3$-$C_6$ alkenyl; $C_5$ or $C_6$ cycloalkyl; benzyl; phenyl; $-(CH_2)_mCO_2R_3$, wherein $R_3$ is hydrogen or $C_1$-$C_5$ alkyl, and m is an integer of from 1 to 4; $-(CH_2)_nA$, wherein A is —OH or —N(RHD 4)$_2$, wherein $R_4$ is $C_1$–$C_3$ alkyl, and n is an integer of from 2 to 6; or —$CH_2CF_3$;

$R_2$ is chlorine or bromine;

each of $Y_1$ and $Y_2$ which may be the same or different, is hydrogen; $C_1$–$C_5$ alkyl; $C_2$–$C_8$ alkenyl; halogen; —$OR_5$, wherein $R_5$ is hydrogen, $C_1$–$C_8$ alkyl or —$(CH_2)_q$-phenyl, wherein q is an integer of from 1 to 4; —$CO_2R_6$, wherein $R_6$ is hydrogen or $C_1$–$C_5$ alkyl; —$N(R_7)_2$, wherein $R_7$ is $C_1$–$C_4$ alkyl; or —$SR_8$, wherein $R_8$ is $C_1$–$C_4$ alkyl; and $Y_3$ is —$CO_2R_6$, wherein $R_6$ is as defined above;

or a pharmaceutically acceptable salt thereof.

4. The pyridazinone according to claim 2, wherein $R_1$ is hydrogen; $R_2$ is chlorine or bromine; each of $Y_1$ and $Y_2$ which may be the same or different, is hydrogen, —$OR_5$ (wherein $R_5$ is hydrogen or $C_1$–$C_7$ alkyl, benzyl or phenethyl); and $Y_3$ is —$OR_5$ (wherein $R_5$ is hydrogen or $C_1$–$C_7$ alkyl, benzyl or phenethyl).

5. A 3(2H)pyridazinone of the formula:

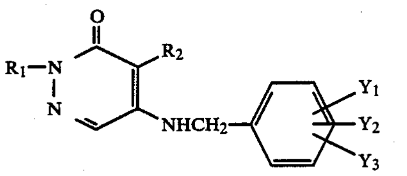

wherein $R_1$ is hydrogen; methyl; $C_3$–$C_6$ alkenyl; $C_5$ or $C_6$ cycloalkyl; benzyl; phenyl; —$(CH_2)_mCO_2R_3$, wherein $R_3$ is hydrogen or $C_1$–$C_5$ alkyl, and m is an integer of from 1 to 4; —$(CH_2)_nA$, wherein A is —OH or —$N(R_4)_2$, wherein $R_4$ is $C_1$–$C_3$ alkyl, and n is an integer of from 2 to 6; or —$CH_2CF_3$;

$R_2$ is chlorine or bromine;

each of $Y_1$ and $Y_2$ which may be the same or different, is hydrogen; $C_1$–$C_5$ alkyl; $C_2$–$C_8$ alkenyl; halogen; —$OR_5$, wherein $R_5$ is hydrogen, $C_1$–$C_8$ alkyl or —$(CH_2)_q$-phenyl, wherein q is an integer of from 1 to 4; —$CO_2R_6$, wherein $R_6$ is hydrogen or $C_1$–$C_5$ alkyl; —$N(R_7)_2$, wherein $R_7$ is $C_1$–$C_4$ alkyl; or —$SR_8$, wherein $R_8$ is $C_1$–$C_4$ alkyl; and $Y_3$ is —$N(R_7)_2$, wherein $R_7$ is as defined above;

or a pharmaceutically acceptable salt thereof.

6. A 3(2H)pyridazinone of the formula:

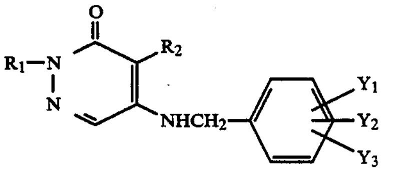

wherein $R_1$ is hydrogen; methyl; $C_3$–$C_6$ alkenyl; $C_5$ or $C_6$ cycloalkyl; benzyl; phenyl; —$(CH_2)_mCO_2R_3$, wherein $R_3$ is hydrogen or $C_1$–$C_5$ alkyl, and m is an integer of from 1 to 4; —$(CH_2)_nA$, wherein A is —OH or —$N(R_4)_2$, wherein $R_4$ is $C_1$–$C_3$ alkyl, and n is an integer of from 2 to 6; or —$CH_2CF_3$;

$R_2$ is chlorine or bromine;

each of $Y_1$ and $Y_2$ which may be the same or different, is hydrogen; $C_1$–$C_5$ alkyl; $C_2$–$C_8$ alkenyl; halogen; —$OR_5$, wherein $R_5$ is hydrogen, $C_1$–$C_8$ alkyl or —$(CH_2)_q$-phenyl, wherein q is an integer of from 1 to 4; —$CO_2R_6$, wherein $R_6$is hydrogen or $C_1$–$C_5$ alkyl; —$N(R_7)_2$, wherein $R_7$ is $C_1$–$C_4$ alkyl; or —$SR_8$, wherein $R_8$ is $C_1$–$C_4$ alkyl; and $Y_3$ is —$SR_8$, wherein $R_8$ is as defined above;

or a pharmaceutically acceptable salt thereof.

7. A 3(2H)pyridazinone of the formula:

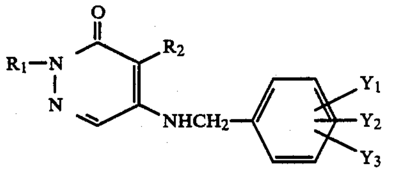

wherein $R_1$ is hydrogen; methyl; $C_3$–$C_6$ alkenyl; $C_5$ or $C_6$ cycloalkyl; benzyl; phenyl; —$(CH_2)_mCO_2R_3$, wherein $R_3$ is hydrogen or $C_1$–$C_5$ alkyl, and m is an integer of from 1 to 4; —$(CH_2)_nA$, wherein A is —OH or —$N(R_4)_2$, wherein $R_4$ is $C_1$–$C_3$ alkyl, and n is an integer of from 2 to 6; or —$CH_2CF_3$;

$R_2$ is chlorine or bromine;

each of $Y_1$ and $Y_2$ which may be the same or different, is hydrogen; $C_1$–$C_5$ alkyl; $C_2$–$C_8$ alkenyl; halogen; —$OR_5$, wherein $R_5$ is hydrogen, $C_1$–$C_8$ alkyl or —$(CH_2)_q$-phenyl, wherein q is an integer of from 1 to 4; —$CO_2R_6$, wherein $R_6$ is hydrogen or $C_1$–$C_5$ alkyl; —$N(R_7)_2$, wherein $R_7$is $C_1$–$C_4$ alkyl; or —$SR_8$, wherein $R_8$ is $C_1$–$C_4$ alkyl; and $Y_3$ is $C_2$–$C_8$ alkenyl or a pharmaceutically acceptable salt thereof.

8. The pyridazinone according to any of claims 7, 1, 2, 3, 5, or 6, wherein $R_1$ is hydrogen; methyl; allyl; cyclopentyl; benzyl; phenyl; —$(CH_2)_mCO_2R_3$, wherein $R_3$ is hydrogen, methyl, ethyl, t-butyl, and m is an integer of 1 or 2; or —$(CH_2)_nA$, wherein A is hydroxyl or dimethyl amino, and n is an integer which is 2 or 3;

$R_2$ is chlorine or bromine;

each of $Y_1$ and $Y_2$, which may be the same or different, is hydrogen; $C_1$–$C_4$ alkyl; $C_3$–$C_8$ alkenyl; halogen; —$OR_5$, wherein $R_5$ is hydrogen, $C_1$–$C_8$ alkyl, benzyl, or phenethyl; —$CO_2R_6$, wherein $R_6$is hydrogen or $C_1$–$C_4$ alkyl; —$N(R_7)_2$, wherein $R_7$ is methyl or ethyl; or —$SR_8$, wherein $R_8$ is $C_1$–$C_4$ alkyl.

9. The pyridazinone according to claim 2, which is 4-chloro-5-(3,4-dimethoxybenzylamino)-3(2H)pyridazinone, or a pharmaceutically acceptable salt thereof.

10. The pyridazinone according to claim 2, which is 4-bromo-5-(3,4-dimethoxybenzylamino)-3(2H)pyridazinone, or a pharmaceutically acceptable salt thereof.

11. The pyridazinone according to claim 2, which is 4-chloro-5-(3-ethoxy-4-methoxybenzylamino)-3(2H)pyridazinone, or a pharmaceutically acceptable salt thereof.

12. The pyridazinone according to claim 2, which is 4-bromo-5-(3-ethoxy-4-methoxybenzylamino)-3(2H)pyridazinone, or a pharmaceutically acceptable salt thereof.

13. The pyridazinone according to claim 2, which is 4-chloro-5-(3-n-propoxy-4-methoxybenzylamino)-3(2H)pyridazinone, or a pharmaceutically acceptable salt thereof.

14. The pyridazinone according to claim 2, which is 4-bromo-5-(3-n-propoxy-4-methoxybenzylamino)-3(2H)pyridazinone, or a pharmaceutically acceptable salt thereof.

15. The pyridazinone according to claim 2, which is 4-chloro-5-(3-n-butoxy-4-methoxybenzylamino-3(2H)pyridazinone, or a pharmaceutically acceptable salt thereof.

16. The pyridazinone according to claim 2, which is 4-bromo-5-(3-n-butoxy-4-methoxybenzylamino)-3(2H)pyridazinone or a pharmaceutically acceptable salt thereof.

17. The pyridazinone according to claim 2, which is 4-chloro-5-(3-pentyloxy-4-methoxybenzylamino)-3(2H)pyridazinone.

18. The pyridazinone according to claim 2, which is 4-bromo-5-(3-n-pentyloxy-4-methoxybenzylamino)-3(2H)pyridazinone.

19. The pyridazinone according to claim 2, which is 4-chloro-5-(3-n-hexyloxy-4-methoxybenzylamino)-3(2H)pyridazinone.

20. The pyridazinone according to claim 2, which is 4-bromo-5-(3-n-hexyloxy-4-methoxybenzylamino)-3(2H)pyridazinone.

21. The pyridazinone according to claim 2, wherein $R_1$ is hydrogen;

$R_2$ is chlorine or bromine;

each of $Y_1$ and $Y_2$ which may be the same or different, is hydrogen; $C_1$-$C_4$ alkyl; —$OR_5$, wherein $R_5$ is hydrogen, $C_1$-$C_7$ alkyl, benzyl or phenethyl; chlorine or —$SCH_3$; and $Y_3$ is —$OR_5$, wherein $R_5$ is hydrogen, $C_1$-$C_7$ alkyl, benzyl or phenethyl; chlorine or —$SCH_3$.

22. The pyridazinone according to claim 2, wherein $R_1$ is hydrogen;

$R_2$ is chlorine or bromine;

each of $Y_1$ and $Y_2$ which may be the same or different, is hydrogen, $C_1$-$C_4$ alkyl or —$OR_5$, wherein $R_5$ is hydrogen, $C_1$-$C_7$ alkyl, benzyl or phenethyl; and $Y_3$ is —$OR_5$, wherein $R_5$ is hydrogen, $C_1$-$C_7$ alkyl, benzyl or phenethyl.

23. An anti-allergic agent according to any of claims 7, 1, 2, 3, 5 or 6, comprising an effective amount of said 3(2H)pyridazinone;

or a pharmaceutically acceptable salt thereof, and a pharmaceutically acceptable carrier.

24. A method of reducing the incidence or severity of allergy induced in a subject by SRS-A, which comprises administering to said subject an amount effective to reduce the incidence or severity of the allergy of a 3(2H)pyridazinone of the formula:

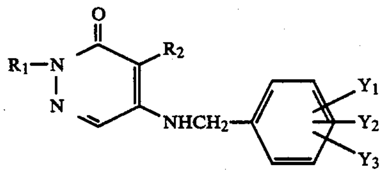

wherein $R_1$ is hydrogen; methyl; $C_3$-$C_6$ alkeyl; $C_5$ or $C_6$ cycloalkyl; benzyl; phenyl; —$(CH_2)_mCO_2R_3$, whererin $R_3$ is hydrogen or $C_1$-$C_5$ alkyl, and m is an integer of from 1 to 4; —$(CH_2)_nA$, wherein A is —OH or —$N(R_4)_2$, wherein $R_4$ is $C_1$-$C_3$ alkyl, and n is an integer of from 2 to 6; or —$CH_2CF_3$;

$R_2$ is chlorine or bromine;

each of $Y_1$ and $Y_2$ which may be the same or different, is hydrogen; $C_1$-$C_5$ alkyl; $C_2$-$C_8$ alkenyl; halogen; —$OR_5$, wherein $R_5$ is hydrogen, $C_1$-$C_8$ alkyl or —$(CH_2)_q$-phenyl, wherein q is an integer of from 1 to 4; —$CO_2R_6$, wherein $R_6$ is hydrogen or $C_1$-$C_5$ alkyl; —$N(R_7)_2$, wherein $R_7$ is $C_1$-$C_4$ alkyl; or —$SR_8$, wherein $R_8$ is $C_1$-$C_4$ alkyl; and $Y_3$ is $C_{1-5}$ alkyl, $C_2$-$C_8$ alkenyl; halogen; —$OR_5$, wherein $R_5$ is as defined above; —$CO_2R_6$, wherein $R_6$ is as defined above; —$N(R_7)_2$, wherein $R_7$ is as defined above; or —$SR_8$, wherein $R_8$ is as defined above;

or a pharmaceutically acceptable salt thereof, and a pharmaceutically acceptable carrier.

25. The pyridazinone according to claim 7, 1, 2 or 6, wherein $R_1$ is hydrogen, allyl or cyclopentyl;

$R_2$ is chlorine or bromine;

each of $Y_1$ and $Y_2$, which may be the same or different, is hydrogen; $C_1$-$C_4$ alkyl; $C_5$-$C_8$ alkenyl; —$OR_5$, wherein $R_5$ is hydrogen, $C_1$-$C_7$ alkyl, benzyl or phenethyl; chlorine; or methyl mercapto.

26. The pyridazinone according to claim 7, wherein $R_1$ is hydrogen, allyl or cyclopentyl;

$R_2$ is chlorine or bromine;

each of $Y_1$ and $Y_2$, which may be the same or different, is hydrogen; $C_1$-$C_4$ alkyl; $C_5$-$C_8$ alkenyl; —$OR_5$, wherein $R_5$ is hydrogen, $C_1$-$C_7$ alkyl, benzyl or phenethyl; chlorine; or methyl mercapto; and $Y_3$ is $C_5$-$C_8$ alkenyl.

27. The pyridazinone according to claim 1, wherein $R_1$ is hydrogen, allyl or cyclopentyl;

$R_2$ is chlorine or bromine;

each of $Y_1$ and $Y_2$, which may be the same or different, is hydrogen; $C_1$-$C_4$ alkyl; $C_5$-$C_8$ alkenyl; —$OR_5$, wherein $R_5$ is hydrogen, $C_1$-$C_7$ alkyl, benzyl or phenethyl; chlorine; or methyl mercapto; and $Y_3$ is chlorine.

28. The pyridazinone according to claim 2, wherein $R_1$ is hydrogen, allyl or cyclopentyl;

$R_2$ is chlorine or bromine;

each of $Y_1$ and $Y_2$, which may be the same or different, is hydrogen; $C_1$-$C_4$ alkyl; $C_5$-$C_8$ alkenyl; —$OR_5$, wherein $R_5$ is hydrogen, $C_1$-$C_7$ alkyl, benzyl or phenethyl; chlorine; or methyl mercapto; and $Y_3$ is —$OR_5$, wherein $R_5$ is hydrogen, $C_1$-$C_7$ alkyl, benzyl or phenethyl.

29. The pyridazinone according to claim 6, wherein $R_1$ is hydrogen, allyl or cyclopentyl;

$R_2$ is chlorine or bromine;

each of $Y_1$ and $Y_2$, which may be the same or different, is hydrogen; $C_1$-$C_4$ alkyl; $C_5$-$C_8$ alkenyl; —$OR_5$, wherein $R_5$ is hydrogen, $C_1$-$C_7$ alkyl, benzyl or phenethyl; chlorine; or methyl mercapto; and $Y_3$ is methyl mercapto.

* * * * *

UNITED STATES PATENT AND TRADEMARK OFFICE

CERTIFICATE OF CORRECTION

PATENT NO. : 4,892,947

DATED : Jan. 9, 1990

INVENTOR(S) : Motoo Mutsukadu, et al

It is certified that error appears in the above-identified patent and that said Letters Patent is hereby corrected as shown below:

Title page:

The second Priority data has been omitted, should read:

--Apr. 27, 1985 [JP] Japan.............60-91612
Apr. 01, 1986 [JP] Japan.............61-75179--

Signed and Sealed this

Sixteenth Day of April, 1991

*Attest:*

HARRY F. MANBECK, JR.

*Attesting Officer*

*Commissioner of Patents and Trademarks*

UNITED STATES PATENT AND TRADEMARK OFFICE
CERTIFICATE OF CORRECTION

PATENT NO. : 4,892,947

DATED : January 9, 1990

INVENTOR(S) : Motoo Mutsukado, et al

It is certified that error appears in the above-identified patent and that said Letters Patent is hereby corrected as shown below:

Column 4, line 15, change "5-position" to --4-position--.

Column 5, lines 3-8, change " 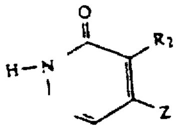 " to

-- 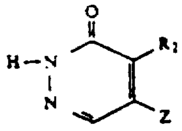 --.

UNITED STATES PATENT AND TRADEMARK OFFICE

CERTIFICATE OF CORRECTION

PATENT NO. : 4,892,947

DATED : January 9, 1990

INVENTOR(S) : Motoo Mutsukado, et al

It is certified that error appears in the above-identified patent and that said Letters Patent is hereby corrected as shown below:

Column 21, heading of Table 8, delete the structure in its entirety and insert therefore -- 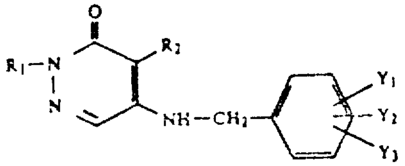 --.

Signed and Sealed this

Eighth Day of October, 1991

Attest:

HARRY F. MANBECK, JR.

*Attesting Officer* *Commissioner of Patents and Trademarks*